United States Patent
Den Brinker et al.

(10) Patent No.: US 12,020,426 B2
(45) Date of Patent: Jun. 25, 2024

(54) DEVICE, SYSTEM AND METHOD FOR PULSATILITY DETECTION

(71) Applicant: KONINKLIJKE PHILIPS N.V., Eindhoven (NL)

(72) Inventors: Albertus Cornelis Den Brinker, Eindhoven (NL); Wenjing Wang, Utrecht (NL); Gerard De Haan, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 448 days.

(21) Appl. No.: 16/071,619

(22) PCT Filed: Feb. 8, 2017

(86) PCT No.: PCT/EP2017/052700
§ 371 (c)(1),
(2) Date: Jul. 20, 2018

(87) PCT Pub. No.: WO2017/137415
PCT Pub. Date: Aug. 17, 2017

(65) Prior Publication Data
US 2019/0050985 A1   Feb. 14, 2019

(30) Foreign Application Priority Data
Feb. 8, 2016   (EP) .................................. 16154665

(51) Int. Cl.
*G06T 7/00*   (2017.01)
*A61B 5/00*   (2006.01)
(Continued)

(52) U.S. Cl.
CPC .......... *G06T 7/0012* (2013.01); *A61B 5/0077* (2013.01); *A61B 5/02416* (2013.01);
(Continued)

(58) Field of Classification Search
CPC ......... G06T 7/0012; G06T 2207/20216; G06T 2207/30076; G06T 2207/30088;
(Continued)

(56) References Cited

U.S. PATENT DOCUMENTS 8,520,074 B2 *   8/2013   Wang .................... G06V 40/103
                                                                    382/192
10,004,427 B1 *  6/2018   Shoeb .................. A61B 5/0816
(Continued)

FOREIGN PATENT DOCUMENTS

DE   2257534 A1 *   5/1973 ........... G06G 7/1921
WO   WO-2010100594 A2 *  9/2010 ........... A61B 5/0064
(Continued)

OTHER PUBLICATIONS

Madhu, et al. "Note on measures for spectral flatness." Electronics Letters, vol. 45, No. 23 ,2009. (Year: 2009).*
(Continued)

*Primary Examiner* — Christopher Koharski
*Assistant Examiner* — Richmond J Van Winter

(57) ABSTRACT

The present invention relates to a device, system and method for pulsatility detection. The proposed device comprises an input interface (30) for obtaining image data of a scene, said image data comprising a time sequence of image frames, an extraction unit (31) for extracting a time-varying signal indicative of a periodic physiological phenomenon from a region of interest of said image data, a transformation unit (32) for transforming said time-varying signal into a spectral signal, a partitioning unit (33) for partitioning the spectral signal into at least an in-band sub-signal covering a first frequency range of said spectral signal and an out-band sub-signal covering a second frequency range of said spectral signal, wherein said first frequency range comprises at least a frequency range of the periodic physiological phe-
(Continued)

nomenon, an analysis unit (34) for separately deriving an in-band measure from the in-band sub-signal and an out-band measure from the out-band sub-signal, the in-band measure and the out-band measure representing a descriptor, and a classifier (35) for classifying said region of interest as a pulsatile region of a living being or as a non-pulsatile region based on the descriptor.

16 Claims, 7 Drawing Sheets

(51) Int. Cl.
*A61B 5/024* (2006.01)
*A61B 5/026* (2006.01)
*A61B 5/0295* (2006.01)
*G06F 18/10* (2023.01)
*G06F 18/2433* (2023.01)

(52) U.S. Cl.
CPC .......... *A61B 5/0261* (2013.01); *A61B 5/0295* (2013.01); *G06F 18/10* (2023.01); *G06F 18/2433* (2023.01); *A61B 5/0075* (2013.01); *A61B 5/02433* (2013.01); *A61B 5/02438* (2013.01); *A61B 5/7203* (2013.01); *A61B 5/7267* (2013.01); *G06T 2207/20216* (2013.01); *G06T 2207/30076* (2013.01); *G06T 2207/30088* (2013.01)

(58) Field of Classification Search
CPC .......... G06T 2207/30201; A61B 5/077; A61B 5/0261; A61B 5/0295; A61B 5/02416; A61B 5/0075; A61B 5/02433; A61B 5/7203; A61B 5/7267; A61B 5/02438; A61B 5/72; A61B 5/0077; G06K 9/6284; G06K 9/6298; G10L 19/0212; G10L 21/038; G10L 19/0204; G10L 19/167; G10L 19/008; H04N 19/63; H04N 9/84; H04N 9/7973; H04N 9/80; H04N 9/83; H04N 9/8355; H04N 9/85; H04N 9/898; H04B 1/667; G06F 17/14; G06F 18/10; G06F 18/2433; G01N 29/46
USPC ................ 386/307, E9.035, E9.047, E9.011, 386/E9.063, E9.049, E9.036, E9.03, 309; 704/229, 205, E19.019, 230, 200.1; 333/177, 204, 108, 106; 375/240.01; 375/240.21; 398/1; 455/228, 45, 260; 379/406.14; 343/840; 381/106
See application file for complete search history.

(56) References Cited

U.S. PATENT DOCUMENTS

| | | | |
|---|---|---|---|
| 2009/0005700 A1* | 1/2009 | Joshi ...................... | A61B 5/389 600/546 |
| 2013/0271591 A1 | 10/2013 | Van Leest | |
| 2013/0296660 A1* | 11/2013 | Tsien ................. | A61B 5/02405 600/407 |
| 2013/0345568 A1 | 12/2013 | Mestha | |
| 2014/0107951 A1* | 4/2014 | Sterenborg ........... | A61B 5/0075 702/50 |
| 2014/0180132 A1* | 6/2014 | Shan ..................... | G06T 7/0012 600/407 |
| 2015/0148636 A1* | 5/2015 | Benaron ............. | A61B 5/02405 600/328 |
| 2015/0250391 A1* | 9/2015 | Kyal ..................... | A61B 5/0077 382/128 |
| 2015/0302158 A1* | 10/2015 | Morris ................... | G06V 10/25 702/19 |
| 2016/0089041 A1* | 3/2016 | Keat ..................... | A61B 5/1032 600/479 |
| 2016/0097716 A1* | 4/2016 | Gulati .................. | A61B 5/1495 250/340 |
| 2016/0226605 A1* | 8/2016 | Olney ..................... | H04L 1/242 |
| 2016/0235312 A1 | 8/2016 | Jeanne | |

FOREIGN PATENT DOCUMENTS

| | | | |
|---|---|---|---|
| WO | 2014/095759 | 6/2014 | |
| WO | 2015/049150 | 4/2015 | |
| WO | WO-2015107268 A1 * | 7/2015 | ......... A61B 5/02416 |
| WO | 2017/137435 | 8/2017 | |

OTHER PUBLICATIONS

Van Luijtelaar, Ron & Wang, W. & Stuijk, Sander & deHaan, Gerard.(2014). Automatic RoI Detection for Camera-Based Pulse-Rate Measurement. 360-374. 10.1007/978-3-319-16631-5_27. (Year: 2014).*

Verkruysse et al., "Remote plethysmographic imaging using ambient light", Optics Express, 16(26), Dec. 22, 2008, pp. 21434-21445.

Gibert et al., "Face detection based on photoplethysmography", 10th IEEE International Conference on Advanced Video and Signal Based Surveillance (AVSS), 2013.

Moço, et al., "Motion robust PPG-imaging through color channel mapping", Biomedical Optical Express, vol. 7, No. 5, pp. 1737-1754, May 2016.

Balakrishnan et al. "Detecting Pulse from Head Motions in Video", IEEE Conference on Computer Vision and Pattern Recognition (CVPR), 2013.

Madhu, et al., "Note on measures for spectral flatness", Electronics Letters, vol. 45, No. 23, 2009.

G. de Haan and A. van Leest, "Improved motion robustness of remote-PPG by using the blood volume pulse signature", Physiol. Meas. 35 1913, 2014.

http://www.dailymail.co.uk/news/article-1345756/Eight-arrested-Hong-Kong-connection-Canadian-people-smuggling-case.html.

Calvo-Gallego, et al., "Automatic ROI for Remote Photoplethysmography using PPG and Color Features", Proceedings of the 10th International Conference on Computer Vision Theory and Applications (VISAPP-2015), pp. 357-364.

Liu, et al., "A New Approach for Face Detection Based on Photoplethysmograhic Imaging", Springer, 2015.

Wlodarczak, et al., "Reality Mining in eHealth" Springer International Publishing Switzerland 2015.

Wang, et al., "Unsupervised Subject Detection via Remote PPG"; IEEE Transactions on Biomedical Engineering, vol. 62, No. 11, Nov. 2015.

Kwon, et al., "ROI analysis for remote photoplethysmography on facial video"; 2015 37th Annual International Conference of the IEEE Engineering in Medicine and Biology Society (EMBC).

Lempe, et al., "ROI Selection for Remote Photoplethysmography"; Bildverarbeitung für die Medizin 2013.

Van Luijtelaar, et al., "Automatic roi detection for camera-based pulse-rate measurement"; The 12th Asian Conference on Computer Vision (ACCV' 14), Int. Workshop on Video Segmentation in Computer Vision, W10—p. 3, Nov. 1-5, 2014, Singapore.

Biswas, et al., "Efficient live face detection to counter spoof attack in face recognition systems"; Proc. of SPIE vol. 9477, 2015.

* cited by examiner

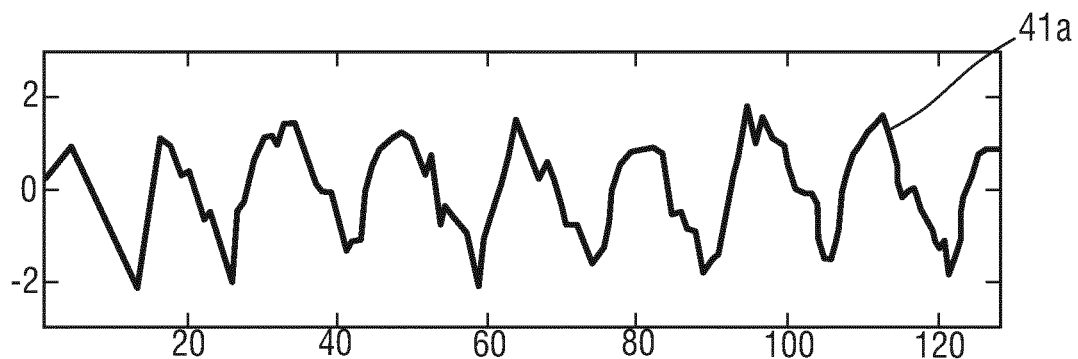
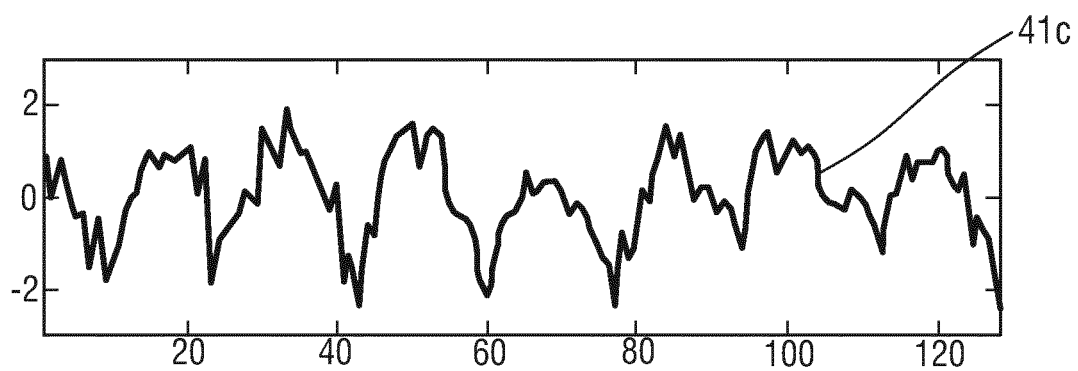
FIG.3A
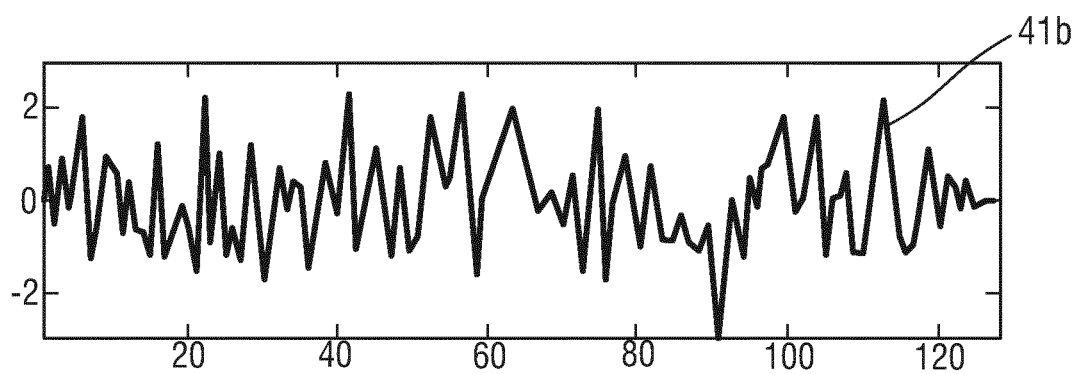
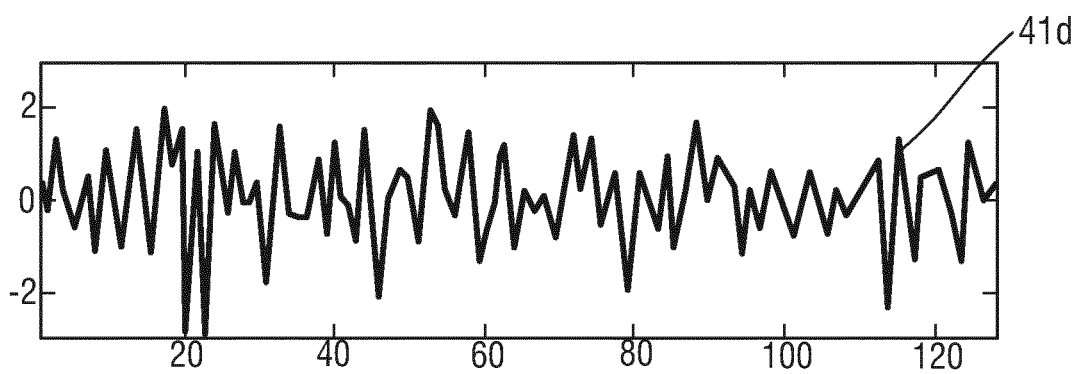
FIG.3B

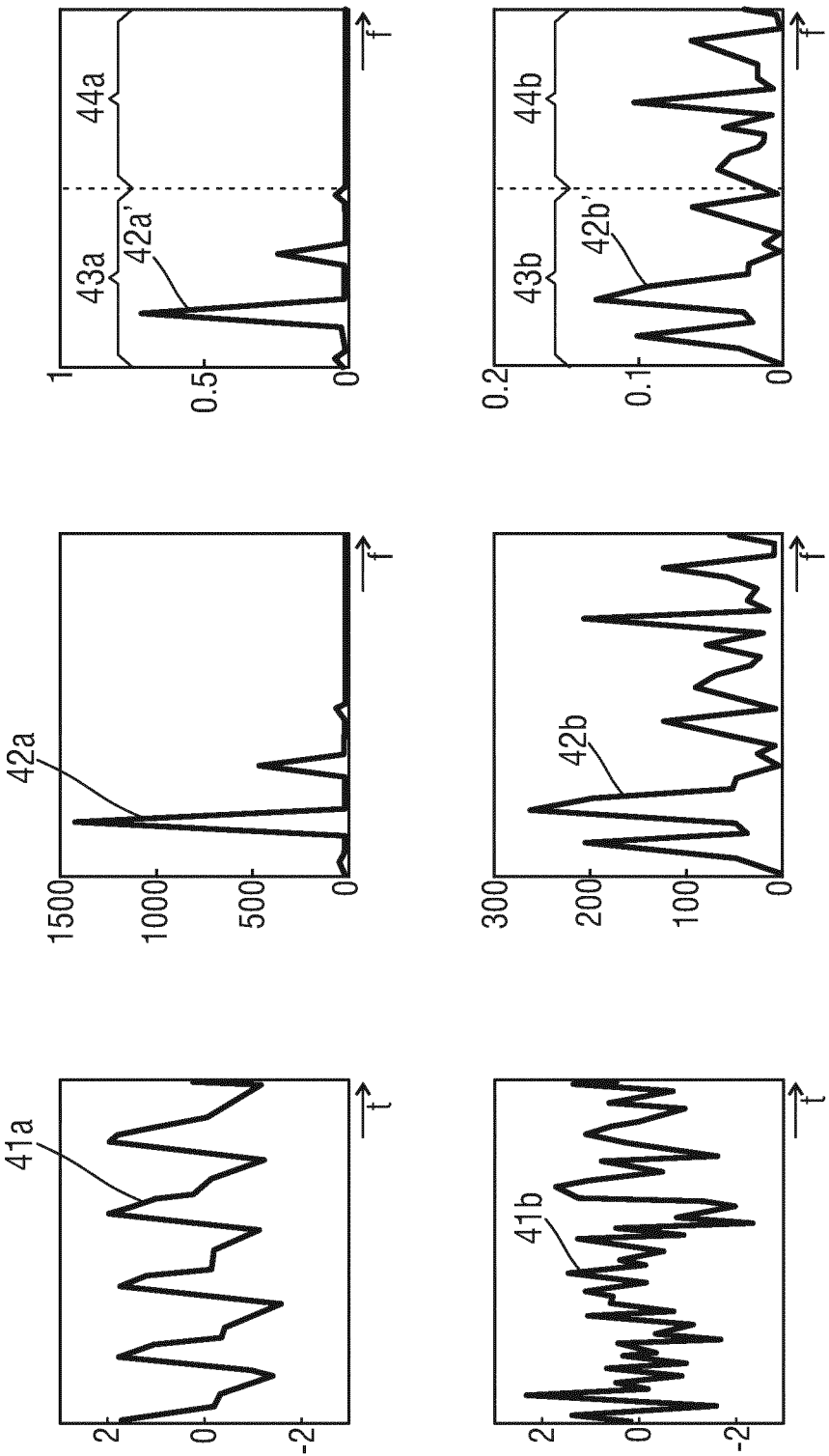

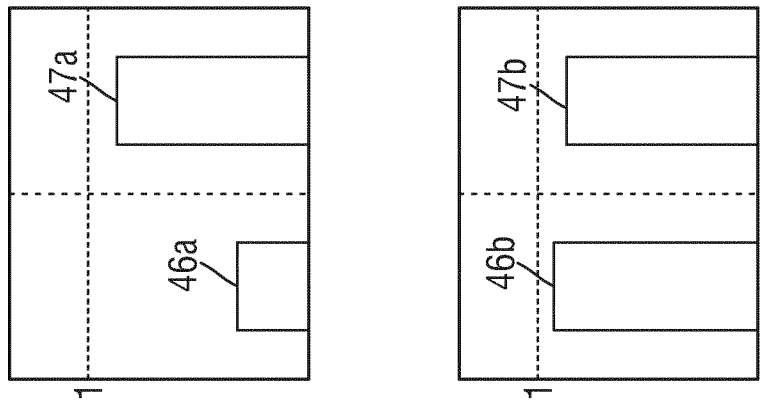
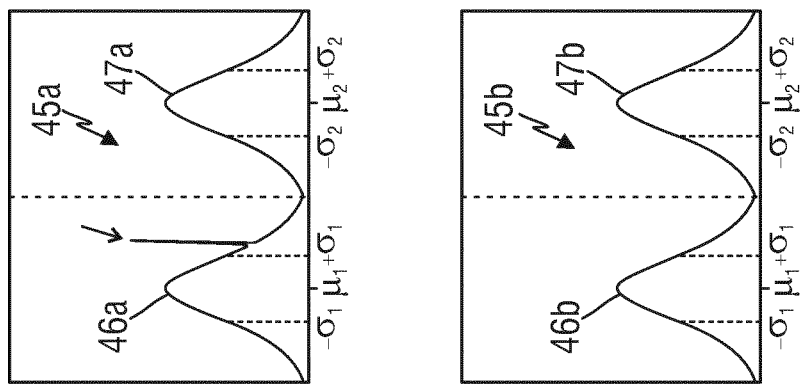
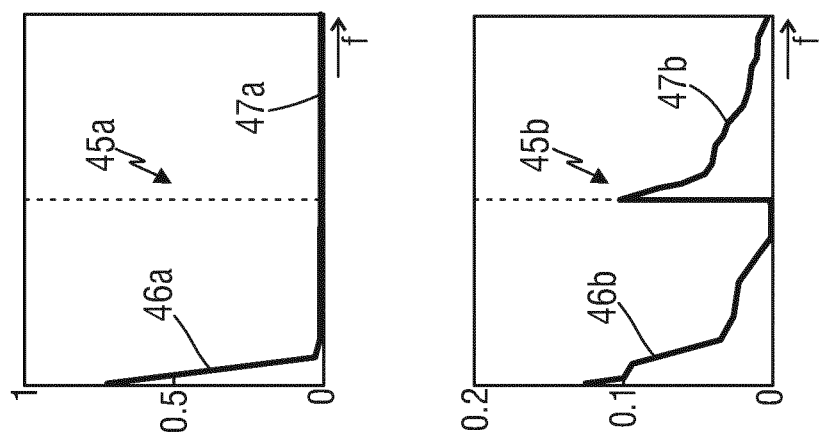
FIG.7
FIG.6
FIG.5

DEVICE, SYSTEM AND METHOD FOR PULSATILITY DETECTION

CROSS REFERENCE TO RELATED APPLICATIONS

This application is the U.S. National Phase application under 35 U.S.C. § 371 of International Application No. PCT/EP2017/052700, filed Feb. 8, 2017, published as WO 2017/137415 on Aug. 17, 2017, which claims the benefit of European Patent Application Number 16154665.0 filed Feb. 8, 2016. These applications are hereby incorporated by reference herein.

FIELD OF THE INVENTION

The present invention relates to a device, system and method for pulsatility detection, in particular for skin detection. Potential applications include determining a region of interest setting for vital signs monitoring or aliveness of a subject.

BACKGROUND OF THE INVENTION

Vital signs of a person, for example the heart rate (HR), the respiration rate (RR) or the arterial blood oxygen saturation (SpO2), serve as indicators of the current health state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides or alternative to information about the heart rate, a PPG waveform can comprise information attributable to physiological phenomena such as the respiration. By evaluating the transmittance and/or reflectivity at different wavelengths (typically red and infrared), the blood oxygen (or other blood gasses/substances) saturation can be determined.

Recently, non-contact, remote PPG (rPPG) devices (also called camera rPPG devices) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well-suited for medical as well as non-medical everyday applications. This technology particularly has distinct advantages for patients with extreme skin sensitivity requiring vital signs monitoring such as Neonatal Intensive Care Unit (NICU) patients with extremely fragile skin, premature babies, or patients with extensive burns.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Apart from the advantage of being fully contactless, cameras (generally called imaging devices) provide 2D information, which allows for a multi-spot and large area measurement, and often contain additional context information. Unlike contact sensors, which rely on the correct placement on a specific measurement point/area, the regions used to measure pulse signals using rPPG technology have to be determined from the actual image. Therefore, accurate detection of skin areas, reliable under greatly varying illumination conditions becomes a crucial part in the processing chain of a camera-based rPPG device and method.

Currently, there are two main approaches known for reliable detection and tracking of a skin areas.

One approach is based on skin color (RGB-based) detection and segmentation. Methods according to this approach are fast in both detection and tracking of areas with skin color. However, they are not robust to changes of ambient light color, which will also change the color of light reflected from a skin area, and are not able to detect skin areas under low illumination conditions or in darkness. Moreover, such methods cannot always differentiate skin from other surfaces with the same color.

Another approach is based on extracted PPG signals (PPG-based), as for example disclosed in Gibert et al., "Face detection based on photoplethysmography", 10th IEEE International Conference on Advanced Video and Signal Based Surveillance (AVSS), 2013. Methods according to this approach are more robust in differentiating real skin areas and areas of other object of the same skin color.

The detection of living tissue or pulsatility from a subject in an image sequence has a range of applications. One application of this is automatic ROI detection for remote photoplethysmography (rPPG), or BCG-motion measurements for patient monitoring, or performing, e.g. vascular, health measurements. Another application is determining a breathing rate of a subject, either from a photoplethysmography-signal, or from quasi-periodic motion caused by respiration. In the latter case the pulsatile signal may be found in non-skin surfaces, e.g. clothes or bedding. It can further be of interest in other technical fields, e.g. in remote gaming applications using camera technology to recognize gestures of the player, face detection, security (robust detection of a person using surveillance cameras and detection of a person wearing a mask or distinguishing real faces from a realistic mask in a camera registration), etc.

It has been shown that the periodic color change itself in acquired images can be used to distinguish between skin and non-skin of a living being. However, particularly for applications with low light level or in the dark, e.g. for night-time patient monitoring, the relatively low amplitude of these absorption variations, particularly in the near-infrared (NIR) wavelength range, is still problematic and causes practical attempts to fail distinguishing skin and non-skin.

SUMMARY OF THE INVENTION

It is an object of the present invention to provide a device and a corresponding method as well as a system which allow for a more reliable, accurate and fast detection of pulsatility, in particular for use in a device and method for detecting vital signs of a subject.

In a first aspect of the present invention a device for pulsatility detection is presented comprising an input interface for obtaining image data of a scene, said image data comprising a time sequence of image frames, an extraction unit for extracting a time-varying signal indicative of a periodic physiological phenomenon from a region of interest of said image data, a transformation unit for transforming said time-varying signal into a spectral signal, a partitioning unit for partitioning the spectral signal into at least an in-band sub-signal covering a first frequency range of said spectral signal and an out-band sub-signal covering a second frequency range of said spectral signal, wherein said first frequency range comprises at least a frequency range of the periodic physiological phenomenon, an analysis unit for separately deriving an in-band measure from the in-band sub-signal and an out-band measure from the out-band sub-signal, the in-band measure and the out-band measure representing a descriptor, and a classifier for classifying said region of interest as a pulsatile region of a living being or as a non-pulsatile region based on the descriptor.

In a further aspect of the present invention a corresponding method is presented.

In a yet further aspect of the present invention a system for pulsatility detection is presented, the system comprising an imaging unit for acquiring image data of a scene and a device for pulsatility detection as disclosed herein based on the acquired image data of the scene.

In yet further aspects of the present invention, there are provided a computer program comprising program code means for causing a computer to carry out the steps of the method as disclosed herein when said computer program is carried out by the computer, as well as a non-transitory computer-readable recording medium that stores therein a computer program product, which, when executed by a computer, causes the method disclosed herein to be performed.

Preferred embodiments of the invention are defined in the dependent claims. It shall be understood that the claimed method, system, computer program and medium can have similar and/or identical preferred embodiments as the claimed device and as defined in the dependent claims.

The present invention is based on the idea to distinguish a pulsatile signal from noise in the frequency domain, more precisely by separately evaluating in-band and out-band sub-signals in the frequency domain signal derived from image data of a scene potentially including a pulsatile area of a living being or even a complete living being or different body parts showing pulsatile and non-pulsatile areas such as skin areas and non-skin areas. The spectral signal is partitioned into at least an in-band sub-signal, comprising a frequency range of at least one vital sign parameter or periodic physiological phenomenon of interest for pulsatility detection, e.g. a pulse or respiratory signal, and an out-band sub-signal covering a second, different frequency range.

Instead of discarding the out-band sub-signal, e.g. by means of a band-pass filter as in the prior art (for a pulse-signal e.g. tuned to a resting heart rate between 0.7 and 2 Hz, corresponding to 42 to 120 beats per minute (bpm)), both in-band and out-band frequency components are preserved in the frequency spectrum. The analysis unit is configured to separately derive an in-band measure from the in-band sub-signal and an out-band measure from the out-band sub-signal. It has been found that thereby, the out-band signal and corresponding out-band measure can serve as a reference for evaluating the in-band sub-signal. The analysis unit is advantageously configured to separately derive the same measure or same type of measure for the in-band sub-signal and for the out-band sub-signal. Hence, the in-band and the out-band signal can be obtained based on the same operations. An advantage is an efficient implementation and calculation, for example, by means of a dedicated ASIC. With a classifier, that is trained accordingly, e.g. using the in-band measure and the out-band measure as an input, a reliable decision can be made whether or not a particular region of interest (ROI) in the image data, e.g. an image segment of the image frames of said image data, shows pulsatility or not.

In other words, the specific characteristics of the pulsatility to be detected, such as a (quasi-)periodic signal due to breathing or cardiac activity, in particular appearing at certain expected frequencies such as heart-rate (HR) or respiration rate (RR) frequencies in an in-band sub-signal as well the absence of thereof in other parts of the spectrum are taken into account.

In particular, characteristics of noise are observable and measureable in a part of the spectral signal where no pulsatility of interest resides (out-band sub-signal). This part of the spectral signal can advantageously be used as a reference and/or for estimating the noise contribution in the other part, i.e., the in-band sub-signal, of the spectrum where pulsatility may reside. Thus, the presence or absence of pulsatility on top of noise in the in-band signal can be identified. Advantageously, the operation under low SNR conditions can be improved, for example for unobtrusive vital signs monitoring at night.

Hence, the proposed device, system and method enable determining whether a 3D time series of image frames (particularly image segments therein) contains alive human tissue or pulsatility, e.g. due to breathing or cardiac activity, or not by substantially extracting a 1D time signal (also called "time-varying signal" herein) from the 3D time series of image frames, transforming the time signal into a transformed spectral signal, partitioning the spectral signal into in-band and out-band sub-signals, separately analyzing the same to obtain a descriptor indicative of the in-band measure and the out-band measure, and classifying the 3D time series of image frames based on the descriptor.

As used herein, an image can not only be understood as being indicative of detected light reflected from a scene in a wavelength range between 300 nm and 1000 nm, or as a thermal image (2000 nm-12000 nm), but more generally from any imaging modality including MRI, CT, etc, and may also include derived images, like a motion-vector fields, e.g. obtained using optical flow.

It shall be noted in this context that at the time of extracting the time-varying signal from a ROI of said image data, e.g. from a ROI in a video sequence, it is not known if the ROI actually shows pulsatility or not. Despite that uncertainty, the ROI is treated as if it contained pulsatility and a time-varying signal is extracted from the ROI with this assumption of being indicative of a periodic physiological phenomenon as conventionally done e.g. with skin regions. In other words, the time-varying signal being indicative of a periodic physiological phenomenon can be considered as a hypothesis to be tested by the device for pulsatility detection, i.e. a signal potentially indicative of a periodic physiological phenomenon. In view of the underlying physiological processes, it shall be understood that a periodic physiological phenomenon as used herein may be subject to variations, e.g. due to heart rate variability or varying breathing rate, and thus also encompasses a quasi-periodic physiological phenomenon.

For the transformation generally any kind of frequency domain transformation, such as a FFT, DCT, wavelet transform, Haar transform, etc. may be used.

Exemplary measures, such as sorted in-band and out-band signals, to be derived by the analysis unit will be explained further below.

According to an embodiment said time-varying signal is one of a photoplethysmography (PPG) signal, a motion signal indicative of the periodic physiological phenomenon, a ballistocardiography (BCG) signal. Alternatively, the time-varying signal can comprise at least one of the aforementioned signals. A PPG signal can be an absorption-based signal indicative of a time-varying absorption, for example caused by subtle color changes in the skin due to pulsating blood flow. The PPG signal can e.g. be indicative of the heart rate or the respiration rate as a vital sign. A motion signal such as a respiratory (chest) motion signal can be indicative of a motion of a subject caused by a physiological phenomenon such as respiration. For example a chest motion of a subject can be monitored. Motion-vector fields can be used as an alternative or in addition to reflection images for example for respiratory-motion signals, but also equally for pulse-motion signals. It is also possible to indirectly obtain the time-varying signal. For example, a (pulsatile/periodic) motion of a blanket can indicative of the respiration of a subject lying in bed. A BCG signal can refer to a pulse-frequent signal caused by motion modulating light. The BCG signal can e.g. be indicative of a cardiac activity such as a cyclical movement of blood from the heart to the head via the abdominal aorta and the carotid arteries which causes the head to move in a periodic motion. Obtaining a BCG signal is exemplarily described by A. Moço, S. Stuijk, and G. de Haan in "Motion robust PPG-imaging through color channel mapping", Biomedical Optical Express, Vol. 7, No. 5, pp. 1737-1754, May 2016. In yet another embodiment, the time-varying signal does not have to be a "brightness" signal indicative of pixel values but could also be a derived signal or image, like a motion vector field obtained from micro-motion of the subject, as disclosed by Balakrishnan et al. in "Detecting Pulse from Head Motions in Video", IEEE Conference on Computer Vision and Pattern Recognition (CVPR), 2013. It shall be understood that the ROI does not have to be skin since a motion may be transferred to e.g. clothes, hair or a blanket covering the subject.

According to an embodiment the device for pulsatility detection is a device for skin detection and said classifier is configured to classify said region of interest as a skin region of a living being or as a non-skin region based on the descriptor. Alternatively or in addition, the device can be configured for detection of pulsatility related to breathing, for example for monitoring a subject located in a bed under a blanket.

According to an embodiment said transformation unit is configured to transform said time-varying signal into a spectral signal without phase information, in particular into a power spectrum or an absolute (amplitude) spectrum, i.e. to convert the complex spectrum to a real signal. The output of a Fourier transform is a complex (real and imaginary parts) signal. If the phase information is not of interest, the norm of the complex samples (length of the vector in the complex plane) may be taken, which is often called the absolute spectrum or amplitude spectrum. By squaring these numbers a power spectrum can be obtained. It is advantageous because it is desired to discriminate between a pulse (which can simply be modeled of a sinusoid with unknown phase and frequency, but will appear as a high amplitude) and noise (which can be modeled as a random (both amplitude and phase) signal, which will in the (sorted or unsorted) spectrum appear as a broad band of frequencies with substantially the same amplitude). In particular when taking sorted spectra as the in-band and out-band measures derived by the analysis unit, they are easy to classify.

In an embodiment, the analysis unit comprises a sorting unit configured to separately sort said in-band sub-signal and said out-band sub-signal to obtain a sorted in-band sub-signal as the in-band measure and a sorted out-band sub-signal as the out-band measure. The sorted spectral sub-signals then represent the descriptor. A pulsatile signal can thus be distinguished from noise in the frequency domain by evaluating, for instance, the distribution of the energy in sorted frequency domain signals derived from image data of a scene potentially including a skin area of a living being or even a complete living being or different body parts showing skin areas and non-skin areas. It has particularly been found that the energy of a pulse signal (in a sorted (or ranked) frequency domain representation) drops faster than the energy of the sorted (or ranked) noise spectrum. With a classifier, that is preferably trained accordingly, i.e., using such ranked spectral sub-signals as an input, a reliable decision can be made whether or not a particular region of interest (ROI) in the image data, e.g. an image segment of the image frames of said image data, shows pulsatility (e.g. a skin area) or not.

Hereby, sorting and ranking shall be understood as synonyms. It means that the order of the frequency samples is changed so that they appear ordered with a decreasing or increasing amplitude, i.e. the frequency samples are re-ordered in frequency direction.

In another embodiment, the analysis unit is configured to separately determine a spectral flatness of the in-band signal as the in-band measure and a spectral flatness of the out-band signal as the out-band measure. The traditional definition of spectral flatness is the ratio of the geometric mean to the arithmetic mean of the magnitude spectrum of the signal. As an alternative to the magnitude spectrum, a power spectrum can be taken as the basis. Furthermore, a spectral flatness measure as proposed by Madhu in "Note on measures for spectral flatness", Electronics Letters, vol. 45, no. 23, 2009, in the different technical field of audio technology can be applied. An advantage of this approach is the robust determination of measures for the in-band and out-band sub-signals and classification with limited computational cost.

In a further embodiment, the analysis unit is configured to separately determine the in-band measure based on an energy of frequency bins of the in-band signal, and the out-band measure based on an energy of frequency bins of the out-band signal. Advantageously, pulsatility can then be detected by comparing the in-band and out-band measures in the classifier. In a further refinement, the analysis unit is configured to separately determine the in band-measure based on a comparison of an energy in frequency bins of the in-band signal to an average energy of the in-band signal; and the out-band measure based on a comparison of an energy in frequency bins of the out-band signal to an average energy of the out-band signal.

In another embodiment, the analysis unit is configured to separately determine the in-band measure and the out-band measure based on statistical outlier detection. For example, a robust estimate such as the median of an energy or amplitude can be made together with a variance estimate.

Amplitudes or energies exceeding those commonly occurring can be determined as outliers and can be indicative of pulsatility. Commonly occurring values can for example be defined as the mean or average value±once or twice the standard deviation. Furthermore, a model of at least one distribution, preferably two distributions for pulsatile and noise, can be used and compared to the in-band sub-signal on the one hand and the out-band sub-signal on the other hand. Hereby, a distribution of values of the out-band signal can be used as the noise model. The distribution of values of the in-band signal can then be compared thereto. In case the distribution of values of the in-band sub-signal matches with the noise model, as determined based on the out-band sub-signal, the region of interest can be classified as a non-pulsatile region, otherwise as a pulsatile region.

In an embodiment, the classifier is configured to classify said region of interest as a pulsatile region of a living being or as a non-pulsatile region based on a comparison of said out-band measure with said in-band measure. The out-band measure can be considered as being indicative of non-pulsatility. In contrast to the in-band sub-signal, the out-band sub-signal does not comprise the frequency range of the (quasi-)periodic physiological phenomenon of interest. The first frequency range is thus different from the second frequency range. Hence, the out-band signal can serve as a reference. Thereby, a robust decision can be reached even for low signal-to-noise ratios.

In a further embodiment, the out-band measure can again be indicative of non-pulsatility and the classifier is configured to determine a decision threshold for classifying said region of interest as a pulsatile region of a living being or as a non-pulsatile region based on the out-band measure. An advantage of this embodiment is that instead of using a fixed decision threshold in the classification, the decision threshold can be adapted based on the out-band measure. For example, in low-signal but also low-noise conditions as indicated by the out-band sub-signal, a lower decision threshold may be set. Thereby a more robust decision can be achieved even for measurements in low-light conditions, for example NIR-based measurements at night.

In an embodiment, the classifier is further configured to determine a consistency metric of the classification of said region of interest as a pulsatile region of a living being or as a non-pulsatile region. The consistence metric can be indicative of a spatial and/or temporal consistency of the classification. For example, it is expected that only connected regions can be a face region, whereas single isolated patches are designated extremely unlikely (dependent on the size of the face or skin portion in the image and actually used ROI size). Similarly for the time domain a (motion compensated) patch producing a pulsatility at a certain moment in time is expected to consistently produce pulsatility. The consistency metric can thus be indicative of a reliability of the classification. The information of other, in particular neighboring, regions can be taken into account, where other regions may refer to other parts of the image and/or other moments in time. This may also be used to steer control settings, e.g. adjust a decision threshold, of the classifier. Optionally such a consistency check may also be implemented as a post-processing.

In an embodiment, the partitioning unit is configured to divide said spectral signal such that the in-band sub-signal covers a lower portion of the frequency range of said spectral signal or a portion of the frequency range around a highest frequency peak of said spectral signal. For instance, the in-band can simply be the lower half of an oversampled signal and the out-band can simply be the upper half of the same oversampled signal. In a more sophisticated version, the in-band may be defined as a window around the highest frequency peak, e.g. with half of the total frequency bins, and the out-band then may be defined by the remaining frequency bins. Other choices for separating the frequency bins are possible as well to define a more accurate in-band, e.g. by choosing likely-pulse spectral components (e.g. only the 20% highest peaks in the frequency domain) as in-band and the remaining spectral components as out-band. Advantageously, the in-band sub-signal covers a first frequency range, wherein the first frequency range comprises a frequency range of at least one vital sign parameter such as the heart rate in a frequency range between 0.7 Hz and 4 Hz (40 bpm (beats per minute) and 240 bpm) and/or the respiration rate between 0.2 Hz and 0.7 Hz (up to 1.6 Hz for infants).

In another embodiment said transformation unit is configured to normalize the spectral signal so that the amplitude or energy (depending on the kind of normalization) of the spectrum does not have an influence on the subsequent evaluation. This makes the spectrum substantially independent of pulse and noise amplitudes in skin and non-skin areas, respectively. The normalization may e.g. be implemented by a division L1- or L2-norm. A practical embodiment may comprise resetting the phase spectrum to a constant value for all frequencies and normalizing the amplitude spectrum to obtain a robust classification.

The device may further comprise a control unit for controlling the transformation unit, the partitioning unit and/or the analysis unit to perform two or more iterations, wherein an output from said analysis unit is used as the input signal for the transformation unit in the next iteration. For example, the control unit is configured to control the transformation unit and a sorting unit of the analysis unit to perform two or more iterations, wherein the sorted spectral signal output from said sorting unit is used the an input signal for the transformation unit in the next iteration. Thus, the iteration acts on the output of the previous iteration, preferably after halving the length of the signal resulting in a multi-scale representation of the spectrum finally used by the classifier. Particularly the first iteration can lead to a relatively peaked signal representing the non-tissue due to resetting the phase of the noise frequency components. Preferably, the length of the spectrum is reduced in the different iterations, i.e., the transformation is performed in different scales resulting in the multi-scale representation, wherein the coarser spectrum (with fewer samples) still describes the same signal, but at a coarser scale.

It has been found that a repetition of the transformation and sorting transforms a (peaked) pulse spectrum into a flat spectrum, while a (relatively flat) noise spectrum is transformed into a peaked spectrum. In the repeated transforms the phase information, the location of the peak, and the amplitude of the spectrum are preferably disregarded. The sorting makes sure that the peak is substantially at the same location improving the classification.

In a further embodiment said classifier is configured to concatenate the measures output from the analysis unit, e.g. the sorted spectral signals output from said sorting unit, in each iteration and use said concatenated signal as descriptor for classifying said region of interest as a pulsatile region of a living being or as non-pulsatile region. For example, in the concatenated sorted spectral signal the peaked portions and flat portions are alternating, wherein the sequence in said alternation is the opposite for a time-varying signal from a pulsatile region compared to a time-varying signal from a non-pulsatile region. Thus, a very reliable classification can be made based on such a said concatenated sorted spectral signal.

Further, in an embodiment said extraction unit is configured to combine, in particular to average, image data values of a group of pixels of said image data per image frame to obtain said time-varying signal from said combined image data values. Hence, the average (combination) over a group of pixels may be taken and the time-evolution of concatenated averages may be considered as the 1D time signal. This improves the reliability of the classification. Basically, a loss of resolution (e.g. of the skin-map) is traded for an improved reliability of the classification because the averaging increases the difference between pulse and noise (by making the time-varying signal less noisy).

The extraction unit may further be configured to combine, in particular to average, image data values of a group of pixels of said image data per image frame at a wavelength or in a wavelength range to obtain said time-varying signal from said combined image data values. Still further, the extraction unit may be configured to combine, per pixel or group of pixels and per image frame, image data values of at least two different wavelength channels as a weighted average to obtain said time-varying signal from said combined image data values. Hence, the average over a group of pixels per wavelength (or color) may be taken, and the time-evolution of concatenated averages may be concatenated per wavelength to obtain the 1D time signal. Hereby, the extraction unit may be configured to compute said weights using a normalized blood volume pulse vector signature based method (i.e. a PBV method), a chrominance based method (i.e. a CHROM method), a blind source separation method (i.e. a BSS method), a principal component analysis (PCA) or an independent component analysis (ICA).

Generally, a PPG signal, as an exemplary time-varying signal, results from variations of the blood volume in the skin. Hence the variations give a characteristic pulsatility "signature" when viewed in different spectral components of the reflected/transmitted light. This "signature" is basically resulting as the contrast (difference) of the absorption spectra of the blood and that of the blood-less skin tissue. If the detector, e.g. a camera or sensor, has a discrete number of color channels, each sensing a particular part of the light spectrum, then the relative pulsatilities in these channels can be arranged in a "signature vector", also referred to as the "normalized blood-volume vector", PBV. It has been shown G. de Haan and A. van Leest, "Improved motion robustness of remote-PPG by using the blood volume pulse signature", Physiol. Meas. 35 1913, 2014, which is herein incorporated by reference, that if this signature vector is known then a motion-robust pulse signal extraction on the basis of the color channels and the signature vector is possible. For the quality of the pulse signal it is essential though that the signature is correct, as otherwise the known methods mixes noise into the output pulse signal in order to achieve the prescribed correlation of the pulse vector with the normalized color channels as indicated by the signature vector.

Details of the PBV method and the use of the normalized blood volume vector (called "predetermined index element having a set orientation indicative of a reference physiological information") have also been described in US 2013/271591 A1, which details are also herein incorporated by reference.

The classifier may further be configured to determine the likelihood that said region of interest is a pulsatile region (e.g. a skin region) of a living being, i.e. the classifier does not only issue a binary decision of whether the region of interest is a skin region or not, but also a likelihood that the region of interest is a skin region.

The classifier may be obtained from supervised learning (e.g. AdaBoost, SVM, etc.), taking the samples of the transformed signal as input (e.g. ranked, normalized frequency bins) and outputting a signal (hard (binary) label, or regression values) identifying the likelihood of an image segment to be alive human tissue or a pulsatile region or not. Further, the classifier may be trained using a dataset of 1D time signals including sinusoids with varying amplitudes, levels of noise, and frequencies in the pulse-rate band to represent the segments containing alive human tissue and/or frequencies in the respiratory-rate band, and noise signals representing segments that do not contain pulsatility e.g. indicative of alive human tissue.

The device may further comprise a segmentation unit for segmenting the image frames of said image data, wherein said extraction unit is configured to extract a time-varying signal from two or more image frame segments for separate subsequent processing. In case the time-varying signal is caused by BCG from reflected light or obtained from a motion vector field, a polarity of the pulsatile time-varying (sub-) signal in different segments can be evaluated before combining them in an output periodic signal. Advantageously, (sub-) signals having same polarity are combined. As shown in the aforementioned paper of Moço et al., a BCG-signal may occur in-phase and in anti-phase, depending on the shading. This concept can also be applied to a motion-field derived time-varying signal, e.g. indicative of a respiratory motion, where a motion-direction may also vary from location to location.

The present invention is preferably used in the context of vital signs acquisition by use of the remote PPG technology. For this purpose said imaging unit is preferably configured to acquire a sequence of images of the scene over time, and said device may further comprise a vital signs detector for detecting vital signs of a subject within the scene based on image information from detected skin areas or areas indicative of a respiratory motion within said sequence of images. Thus, the proposed detection of pulsatile areas may be once or continuously used to detect and/or track pulsatile regions such as skin areas during the acquisition of vital signs.

BRIEF DESCRIPTION OF THE DRAWINGS

These and other aspects of the invention will be apparent from and elucidated with reference to the embodiment(s) described hereinafter. In the following drawings FIGS. 3A and 3B show diagrams illustrating exemplary time-varying signals from skin and non-skin regions for different living beings, FIGS. 4A, 4B, and 4C show diagrams illustrating exemplary signals at the various steps of a method according to an embodiment of the present invention, FIG. 5 shows diagrams illustrating a first analysis approach, FIG. 6 shows diagrams illustrating a second analysis approach, FIG. 7 shows diagrams illustrating a third analysis approach.

DETAILED DESCRIPTION OF EMBODIMENTS

Figure 1:
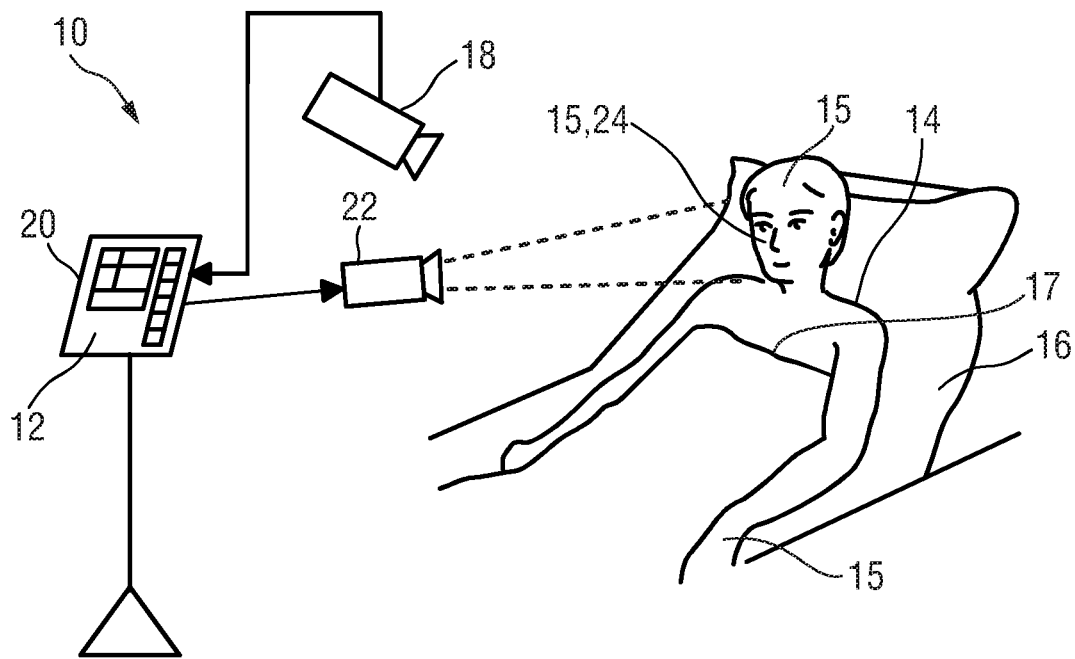
FIG. 1 shows a schematic diagram of a first embodiment of a system according to the present invention.

FIG. 1 shows a schematic diagram of a system 10 according to the present invention including a device 12 for pulsatility detection, in particular for skin detection. The system 10 and device 12 may preferably be used in a device and method for detecting vital signs of a subject 14 from image data including a time sequence of image frames of the subject. The subject 14, in this example a patient, lies in a bed 16, e.g. in a hospital or other healthcare facility, but may also be a neonate or premature infant, e.g. lying in an incubator, or person at home or in a different environment, such as an athlete doing sports.

The imaging unit 18 may include a camera (also referred to as detection unit or as camera-based or remote PPG sensor) for acquiring an image data (also called RGB images, which shall be understood as an image in the wavelength range of visual and/or infrared light) of the scene, in particular for acquiring a sequence of image frames of the subject 14 over time, preferably including skin areas 15 of the subject 14 from which PPG signals can be derived. In an application of the device 12 for obtaining vital signs of the subject 14, the skin area 15 is preferably an area of the face, such as the cheeks or the forehead, but may also be another area of the body with visible skin surface, such as the hands or the arms. In addition or in the alternative, a respiratory motion of the subject 14 may be detected to obtain a time-varying signal, e.g. from subtle respiratory movements caused by of portions of the subject located under a blanket 17. Still further, a BCG (ballistocardiographic) time-varying signal may be obtained e.g. from subtle movements of the head or from movements of the skin near a superficial artery. In the following non-limiting examples, reference will be made to a PPG signal as the time-varying signal. It shall be understood that the teachings apply mutatis mutandis to other types of time-varying signals indicative of a (quasi-)periodic physiological phenomenon.

The image frames captured by the imaging may particularly correspond to a video sequence captured by means of an analog or digital photo sensor, e.g. in a (digital) camera. Such a camera usually includes a photo sensor-array, such as a CMOS or CCD image-sensor, which may also operate in a specific spectral range (visible, nIR) or provide information for different spectral ranges, particularly enabling the extraction of PPG signals. The camera may provide an analog or digital signal. The image frames include a plurality of image pixels having associated pixel values. Particularly, the image frames include pixels representing light intensity values captured with different photosensitive elements of a photo sensor. These photosensitive elements may be sensitive in a specific spectral range (i.e. representing a specific color). The image frames include at least some image pixels being representative of a pulsatile region such as a skin portion of the person. Thereby, an image pixel may correspond to one photosensitive element of a photo-detector and its (analog or digital) output or may be determined based on a combination (e.g. through binning) of a plurality of the photosensitive elements. The disclosure may also be applied to different imaging modalities such as MRI or CT-images.

When using a camera 18 the system 10 may further optionally comprise an illumination unit 22 (also called illumination source or light source or electromagnetic radiator), such as a lamp or LED, for illuminating/irradiating a region of interest 24, such as the skin of the patient's face (e.g. part of the cheek or forehead) and/or a chest region, with light, for instance in a predetermined wavelength range or ranges (e.g. in the red, green and/or infrared wavelength range(s)). The light reflected from said region of interest 24 in response to said illumination is detected by the camera 18. In another embodiment no dedicated light source is provided, but ambient light is used for illumination of the subject 14. From the reflected light only light in a desired wavelength ranges (e.g. green and red or infrared light, or light in a sufficiently large wavelength range covering at least two wavelength channels) may be detected and/or evaluated. In case of using a thermal camera the radiation of the human body can be used directly.

The device 12 in the shown embodiment is further connected to an interface 20 for displaying the determined information and/or for providing medical personnel with an interface to change settings of the device 12, the camera 18, the illumination unit 22 and/or any other parameter of the system 10. Such an interface 20 may comprise different displays, buttons, touchscreens, keyboards or other human machine interface means.

A system 10 as illustrated in FIG. 1 may, e.g., be located in a hospital, healthcare facility, elderly care facility or the like. Apart from the monitoring of patients, the present invention may also be applied in other fields such as neonate monitoring, general surveillance applications, security monitoring or so-called lifestyle environments, such as fitness equipment, a wearable, a handheld device like a smartphone, or the like. The uni- or bidirectional communication between the device 12, the camera 18 and the interface 20 may work via a wireless or wired communication interface. Other embodiments of the present invention may include a device 12, which is not provided stand-alone, but integrated into the camera 18 or the interface 20.

In the following non-limiting example, pulsatility detection will be described with reference to skin detection, in particular based on pulsatility due to heart beats. The teachings of the present disclosure can be applied accordingly to pulsatility detection based on other physiological processes such as respiration.

Figure 2:
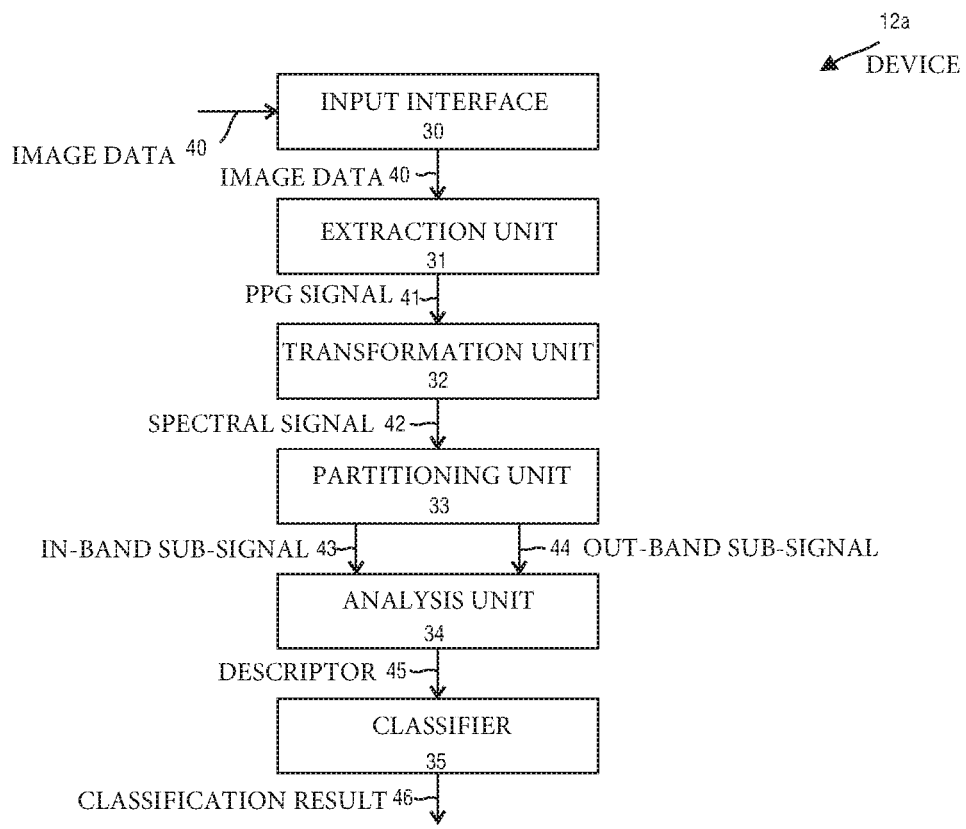
FIG. 2 shows a schematic diagram of a first embodiment of a device according to the present invention.

FIG. 2 shows a schematic diagram of a first embodiment of a device 12a according to the present invention, which may be used as device 12 in the system 10 shown in FIG. 1. For deriving one or more vital signs of the subject 14 a skin area of the subject shall be found in the image data. For this purpose, the proposed device 12a comprises an input interface 30 for obtaining image data 40 of a scene, said image data comprising a time sequence of image frames acquired by the imaging unit 18. An extraction unit 31 extracts a PPG signal 41 from a region of interest of said image data, wherein said region of interest may be a single pixel or a group of pixels or an area resulting from a segmentation of one or more image frames. A transformation unit 32 transforms said PPG signal 41 into a spectral signal 42. A partitioning unit 33 partitions the spectral signal into at least an in-band sub-signal 43 covering a first frequency range of said spectral signal and an out-band sub-signal 44 covering a second frequency range of said spectral signal, wherein said first frequency range comprises a frequency range of at least one vital sign parameter. An analysis unit 34 is configured to separately derive an in-band measure from the in-band sub-signal and an out-band measure from the out-band sub-signal, the in-band measure and the out-band measure representing a descriptor 45. Finally, a classifier 35 classifies said region of interest as a pulsatile region of a living being or as a non-pulsatile region based on the descriptor. The classifier can then issue a corresponding classification result 46, which may be a binary decision (e.g. indication that the region of interest is a pulsatile region such as a skin area or not) or a likelihood that the region of interest is a pulsatile region or not.

The units 30 to 34 may be configured as dedicated hardware elements, but may also be configured as processor or computer, which is programmed accordingly. The device 12*a* may be configured as integrated device including all its elements and units, e.g. in a common housing (e.g. in a common housing of the imaging unit 18) or as distributed device, as shown in FIG. 1, in which the elements and units may be distributed, i.e. implemented as separate elements and units arranged at different positions.

FIGS. 3A and 3B show diagrams illustrating exemplary time-varying signals, here PPG signals 41 from skin and non-skin regions for different living beings. In particular, FIG. 3A shows a pulse signal 41*a* from a first subject (e.g. an adult) and a pulse signal 41*c* from a second subject (e.g. a neonate). As can be seen, the pulse signals from different subjects are different. Further, even the pulse signal from a single subject is time-varying (e.g. in phase). Although the pulse generally has a clear periodic component, there may be variations in amplitude, phase and even frequency (e.g. heart rate variability), and typically the signal will also suffer from sensor noise and may be distorted by subject motion. FIG. 3B shows a noise signal 41*b* from the first subject (e.g. an adult) and a noise signal 41*d* from the second subject (e.g. a neonate). As can be seen, noise signals are irregular/erratic signals that cannot be learned, while also pulse signals exhibit significant variability. Hence, one idea is to transform obtained time-varying signals into a different representation that allows supervised learning.

Considering pulse and noise as two classes, the transformed representation (e.g. the descriptor) should preferably eliminate three properties of time-varying signals. The descriptor should preferably be invariant to phase changes of pulse/noise, i.e. pulse at different moments. Further, the descriptor should preferably not depend on the amplitude of pulse/noise. Still further, the descriptor should preferably be independent of varying frequencies in pulse/noise, i.e. different subjects. Further advantageously the same measure or same type of measure can be derived for the in-band sub-signal and for the out-band sub-signal. Thereby, the implementation and computational complexity may be reduced, which can also be advantageous for reducing the power consumption of wearable devices.

Given above requirements, the following exemplary first approach can be applied to the time-varying PPG signals 41, which is illustrated by use of FIG. 4 showing a diagram illustrating exemplary signals at the various steps of a method according to a first embodiment. In a first step, spectrum boosting can optionally be applied to the PPG signals 41 (for illustration, a pulse signal 41*a* and a noise signal 41*b* are shown in FIG. 4A) by the transformation unit 32. Based on the valid assumption that pulse is a periodic signal, the transformation unit 32 transforms the PPG signal 41 from time domain to frequency domain for analysis, for instance by use of a Fourier Transform (FT). The transformed pulse 42*a* shown in FIG. 4B presents a significant peak in the frequency spectrum, whereas the transformed noise 42*b* shown in FIG. 4B is an irregular signal that does not show such a pattern. Hereby, the Fourier Transform (or Fast Fourier Transform; FFT) can be replaced by a Discrete Cosine Transform (DCT), a Discrete Sine Transform (DST), a Wavelet Transform, or a Haar Transform, etc.

Using the FT can be written as:

$$\vec{F}^L = \mathcal{F}(\vec{P}^L), \quad (1)$$

with $\vec{P}^L$ the PPG signal with length L for $\vec{F}^L$ Fourier transform (e.g., L=64); $\mathcal{F}(:)$ denotes the FT operation. The real and imaginary parts of $\vec{F}^L$ contain varying phase information, which can be eliminated by just using the amplitude or power spectrum. Preferably, the power spectrum is used because it generally boosts the frequency peak of pulse and suppresses the noise. Since $\vec{F}^L$ is a mirrored spectrum with half redundancy, it is halved before deriving the power spectrum:

$$S^{L/2} = \vec{F}^{1 \rightarrow L/2} \odot \text{conj}(\vec{F}^{1 \rightarrow L/2}), \quad (2)$$

where conj(·) denotes the conjugation; ⊙ denotes the element-wise product. In $S^{L/2}$, the phase information disappears, while the frequency peak of pulse is boosted as compared to that of noise, as shown in FIG. 4B.

In a next step, spectrum normalization may optionally be performed by the transformation unit 32. This normalization makes the spectrum substantially independent of pulse and noise amplitudes in skin/non-skin areas, respectively. The spectrum amplitudes are still variant in $S^{L/2}$, which are normalized as:

$$\overline{S}^{L/2} = \frac{S^{L/2}}{\|S^{L/2}\|_p}, \quad (3)$$

where $\|\cdot\|_p$ denotes the Lp-norm. It can either be the L1-norm or L2-norm. The normalization of the standard deviation is not preferred, since only the absolute energy information shall be eliminated, but the variation should remain within the spectrum for distinguishing pulse and noise. In an exemplary embodiment the L2-norm is used, because the normalized $\overline{S}^{L/2}$ is independent of spectrum amplitude, whereas the relative energy distribution of its entries remains, as shown in FIG. 4C for a normalized spectral pulse signal 42*a*' and a normalized spectral noise signal 42*b*'.

In a next step, the spectral signal 42*a*' is partitioned by the partitioning unit 33 into an in-band sub-signal 43*a* covering a first frequency range of said spectral signal 42*a*' and an out-band sub-signal 44*a* covering a second frequency range of said spectral signal 42*a*'. In the shown example, the partitioning unit 33 is configured to divide said spectral signal such that the in-band sub-signal covers a lower portion of the frequency range of said spectral signal and the out-band signal covers an upper portion of the frequency range of the spectral signal, for example an lower half and an upper half respectively. Hereby, first frequency range comprises a frequency range of at least one vital sign parameter such as the heart rate in a frequency range of e.g. 0.7 to 4 Hz and/or the respiratory rate in a frequency range of e.g. 0.2 to 0.7 Hz. Similarly for said spectral signal 42*b*', resulting in an in-band sub-signal 43*b* and an out-band sub-signal 44*b*.

Hence, in view of the frequency variance, $\overline{S}^{L/2}$ us not directly used for classification yet. However, although different individuals have different heart rates, their pulse frequencies are mostly peaked and concentrated in a certain (lower) band, i.e., [40, 240] beats per minute (bpm) or [0.7, 4] Hz, whereas the background (non-skin) signals are usually white noise that spread into the high-frequency band. To this end, the $\overline{S}^{L/2}$ is divided by the partitioning unit 33, e.g. halved into two halves (also called sub-signals), preferably into lower and upper parts to approximate the "in-band" and "out-band" frequencies, where the pulse-related property is implicitly exploited here.

In a next step, an in-band measure and an out-band measure are derived separately from the in-band sub-signal 43 and the out-band sub-signal 44, respectively by the analysis unit 34, the in-band measure and the out-band measure representing a descriptor 45. In the given example, the analysis unit comprises 34 comprises a sorting unit configured to separately sort said in-band sub-signal 43 and said out-band sub-signal 44 to obtain a sorted in-band sub-signal as the in-band measure and a sorted out-band sub-signal as the out-band measure. In this step spectrum sorting is performed by the sorting unit of the analysis unit 34.

In accordance with the first embodiment, a frequency dependency can be eliminated in that, the divided spectrums are sorted and then concatenated as:

$$\hat{S}^{L/2}=[\text{sort}(\overline{S}^{1 \to L/4}), \text{sort}(\overline{S}^{L/4 \to L/2})], \quad (4)$$

where sort(·) denotes sorting the spectrum entries for example in a descending order of amplitude/energy. In $\hat{S}^{L/2}$, the frequency variance in pulse and noise are eliminated, but their essential differences in the lower band and upper band are preserved, as shown in FIG. 5 showing a sorted spectral pulse signal as the descriptor 45a and a sorted spectral noise signal as the descriptor 45b. Hence, in this step a ranking (sorting) procedure is essentially performed acting on the frequency bins.

Hereby, the in-band measure 46a, 46b and the out-band measure 47a, 47b together represent a descriptor 45a, 45b of the original PPG signal 41a, 41b which is then provided to the classifier 35 for classifying said region of interest as a pulsatile region (pulse signal in upper row of FIG. 4) of a living being or as a non-pulsatile region (noise signal in lower row of FIG. 4). As can be seen from FIG. 5, the fall-off of the sorted amplitudes is different in case of pulsatility 45a and noise 45b. In particular the comparison between the in-band measure 46a, 46b and the out-band measure 47a, 47b clearly shows the different characteristics which are exploited in the classification.

An essential difference between the proposed approach and known approaches is that, instead of discarding the non-pulsatile component, the out-band signal is used for improved signal processing. This is particularly advantageous under low-light conditions. In other words, the solution proposed herein uses e.g. the raw signal or more precisely pulse and noise or the in-band and out-band sub-signals, where vital sign and non-vital sign (e.g. HR and non-HR) components are preserved in the frequency spectrum. Hereby, the out-band signal can be considered as a reference.

In contrast, known approaches tend to discard out-band signals, e.g. by means of a band-pass filter, to separate pulse and noise, whereas the proposed approach exploits both the in-band sub-signal and the out-band sub-signal for classification. In the given example, all the entries in the sorted in-band and out-band spectrum may thus be used for classification. The sorted spectra as the in-band and out-band measures can in fact be considered as a shape descriptor.

Essentially, according to this first embodiment, the phenomenon is exploited that the energy of a pulse signal (in the ranked frequency spectrum 45a) drops faster than the energy of the ranked noise spectrum 45b. With a trained classifier 35 using these ranked spectra as input an optimal decision can be obtained. In other words, in the above illustrated first embodiment the sorted spectral signals 45a, 45b are used by the classifier 35 to decide if the respective region of interest in the original image data is a pulsatile region of a living being or is a non-pulsatile region.

The approach proposed herein can also be seen as a hypothesis testing. Pulsatility essentially implies the presence of a quasi-periodic signal such as a periodic pulse signal due to cardiac activity or respiration. In pulsatility detection, however, it is not mandatory to determine a precise value such as a heart rate, instead a determination with respect to presence or absence of pulsatility is of interest. Hence, the essential hypothesis to be tested is if there is pulsatility in an expected spectral range, i.e., within the first frequency range covered by the in-band signal, or not. The second frequency range (which is different from the first frequency range, in particular non-overlapping), covered by the out-band sub-signal, can thus serve as a reference for the hypothesis testing. For the second frequency range, the opposite expectation exists, namely that no pulsatility is present.

In other words, the characteristics of noise are observable and measureable in a part of the spectrum where no significant contributions from vital signs are present, typically above a frequency range of interest for vital signs. This part of the spectrum (out-band) can therefore be used as a reference for estimating the noise contribution in the other part of the spectrum (in-band) where the pulsatility may reside.

FIG. 6 shows diagrams illustrating a second analysis approach. The first processing steps may correspond to the one described with reference to FIG. 4A and FIG. 4B and the optional normalization of FIG. 4C. The second approach can also be referred to as a statistical approach or model-based statistical approach. The PPG signal shown in FIG. 4A can be considered as a time-discrete signal x, wherein the signal x depends on an index k with k=1 . . . K. This signal is transformed in the frequency domain as shown in FIG. 4B yielding a spectral representation X. The signal X is a function of frequency f (or frequency bin) and denoted as X(f). The frequencies in the in-band sub-signal are denoted by fi, those in the out-band sub-signal by fo. In the given example, it is assumed that the noise in the PPG signal (see FIG. 4A) is independently distributed Gaussian white noise. The power spectral density function (PSDF) of the signal is then a Chi2 distribution with two degrees of freedom. The PSDF samples in the out-band sub-signal can then be used to estimate the parameters of the distribution. This is exemplarily indicated by the mean value $\mu_2$ and standard deviation $\sigma_2$ for the out-band signal. Hereby, the distribution as determined based on the out-band sub-signal can serve as the out-band measure. Alternatively, the mean value and/or the standard deviation can serve as the out-band-measure.

Next, a test can be run which of the samples of the in-band sub-signal are likely to follow this distribution, i.e., the same distribution as the out-band sub-signal, and which samples are not are statistically outliers. In particular outliers in the positive range (indicated by the arrow on curve 46a in FIG. 6) would indicate tonality. For example, it can be tested if there exists an fh with PSDF X(fh) such that the probability p(X(fh))>T, where T is a threshold (e.g. T=0.95), then pulsatility is detected. It is to be understood that other assumptions can be made on the noise signal leading to other distributions for the samples of the PSDF noise part, but the principle remains the same: an outlier test can be done in the in-band (fh) based on a parameterized distribution where the parameters are estimated from the out-band sub-signal. Alternatively, such statistical tests can be on the spectral amplitudes instead of the PSDF.

Hence, the distribution (or parameters indicative thereof) as determined based on the out-band sub-signal can be used as the out-band measure. Correspondingly, a distribution (or parameters indicative thereof) as determined based on the in-band sub-signal can be used as the in-band measure. Such an in-band and out-band measure represent a descriptor which is then used by the classifier.

Exemplary distributions as the in-band measure 46a, 46b and the out-band measure 47a, 47b are illustrated in FIG. 6. As can be seen the measures for the noise signal (lower graph) show good correspondence, i.e., the signal can be classified as a non-pulsatile region. On the other hand, the measures for the pulse signal (upper graph) show different distributions, i.e., the signal can be classified as a pulsatile region.

In case of incomplete knowledge of the underlying distribution, a further option is to resort to distance methods. From the out-band sub-signal, estimates are made of the average m (e.g. mean or median) and the range r (e.g. std or quartile range) of X. Next the samples in the HR band are expressed in unit deviations from the average (mean or median) $\mu$ divided by the range (std or quartile range): $Z(fi)=(X(fh)-\mu)/r$. Thereby, the value Z essentially expresses a normalized distance. Values Z exceeding a predetermined threshold are indicative of pulsatility. Thresholding on the Z could then be used by the classifier for pulsatility detection.

Having identified frequencies fh for which the probability or distance exceeds the threshold, it can further be checked for the remaining samples how well these conform the distribution or distance measure as described in the out-band sub-signal, i.e., how similar the in-band and out-band measures are for such further samples. If there is a dissimilarity, then the usage of the data from the out-band sub-signal band to identify pulsatility may not be reliable. In this way an additional validation step can be implemented.

FIG. 7 shows diagrams illustrating a further analysis approach. The first processing steps may correspond to the one described with reference to FIG. 4A and FIG. 4B and optionally the normalization of FIG. 4C. In the example, the analysis unit 34 is configured to separately determine a spectral flatness of the in-band signal as the in-band measure and a spectral flatness of the out-band signal as the out-band measure. The spectral flatness as used herein can be defined as the geometric mean over the arithmetic mean of the spectrum values or variants thereof as described in Madhu in "Note on measures for spectral flatness", Electronics Letters, vol. 45, no. 23, 2009, the content of which is included herein by reference. In case of a pulse signal the in-band sub-signal, shows distinct frequency peaks (see FIG. 4B) and thus has a lower spectral flatness as the in-band measure 46a in FIG. 7. On the other hand the out-band signal does not show such pulsatile peaks and therefore has a higher spectral flatness as the out-band measure 47a in FIG. 7. On the other hand, as shown in the lower graph in FIG. 7, in case of absence of pulsatility, the two flatness estimates for the in-band measure 46b and the out-band measure 47b are assumed to be similar. The classifier can thus easily and reliably compare these in-band and out-band measures in order to classify the region of interest from which the PPG signal 41a, 41b (see FIG. 4A) has been obtained as a pulsatile region of a living being or as a non-pulsatile region.

Alternatively, also a derived measure such as a ratio of the two spectral flatness-metrics can be used. Furthermore, additional data such as a spectral flatness over the full band may be used by the classifier to further improve the reliability. Additional transformations such as logarithmic scaling of a flatness measure may be applied.

Optionally, one or more of the above approached can be combined e.g. using a trained classifier on a combination of one or more of (i) a sorting/ranking-based approach, (ii) the probability/probabilities stemming from a parameterized statistical model, (iii) a distance or distances, and (iv) spectral flatness measures. Any combination of the original parameters, transformed parameters, and/or derived parameters may be fed to classifier which is trained accordingly.

Figure 8:
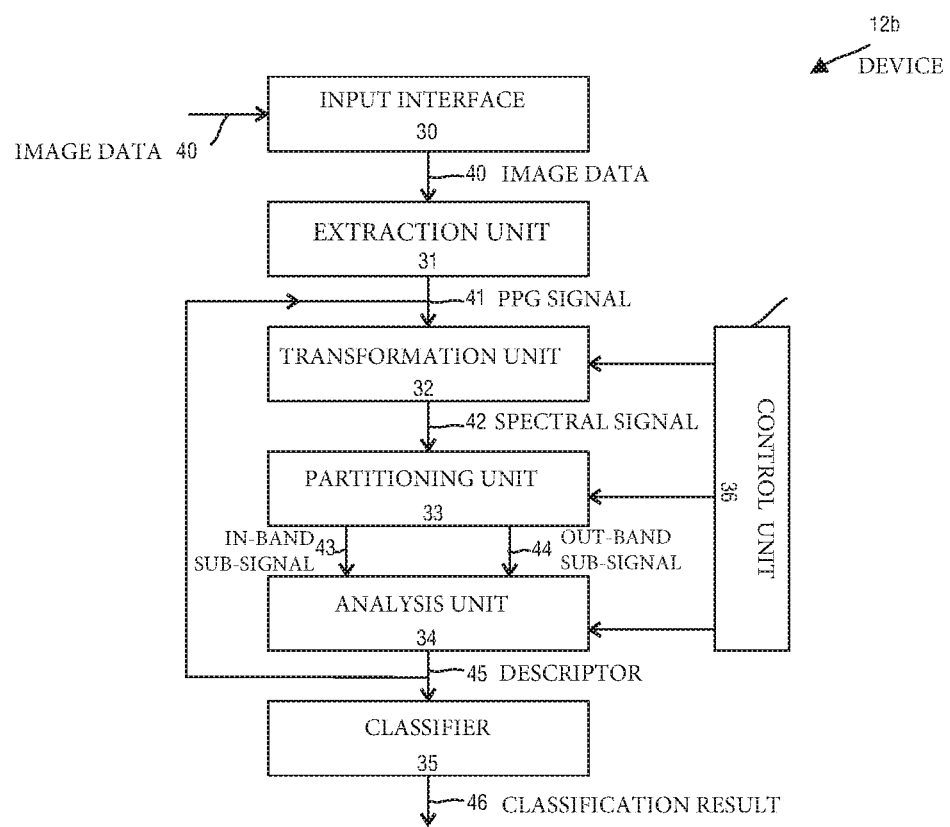
FIG. 8 shows a schematic diagram of a second embodiment of a device according to the present invention.

FIG. 8 shows a schematic diagram of a second embodiment of a device 12b according to an aspect of the present invention. In this embodiment a control unit 36 is provided for controlling said transformation unit 32, said partitioning unit 33 and said analysis unit 34 to perform two or more iterations. In the shown example, the analysis unit 34 comprises a sorting unit and the sorted spectral signal 45 output from said sorting unit is used as input PPG signal 41' for the transformation unit 32 in the next iteration. Thus, according to this embodiment a multiscale iteration may be performed as will be explained in the following.

With the first embodiment of the device 12a a transformed signal $\hat{S}^{L/2}$ is obtained given the input PPG signal $\vec{P}^L$, where pulse and noise have self-unified but mutually different interpretations. If the descriptor for pulse and noise is compared, the pulse-descriptor has a salient feature (e.g., peak at first location), whereas the noise does not. To obtain better classification performance, the descriptors from different classes require large between-class variance, i.e. pulse and noise are easily distinguishable. This can be improved by iterating the procedure (boost, normalize, sort). Now the relatively flat noise spectrum translates into a clear peak, while the peaked pulse spectrum translates into a relatively flat result. The two iterations combined provide an anti-phase pattern between two classes, which lead to easier separation.

Figure 9:
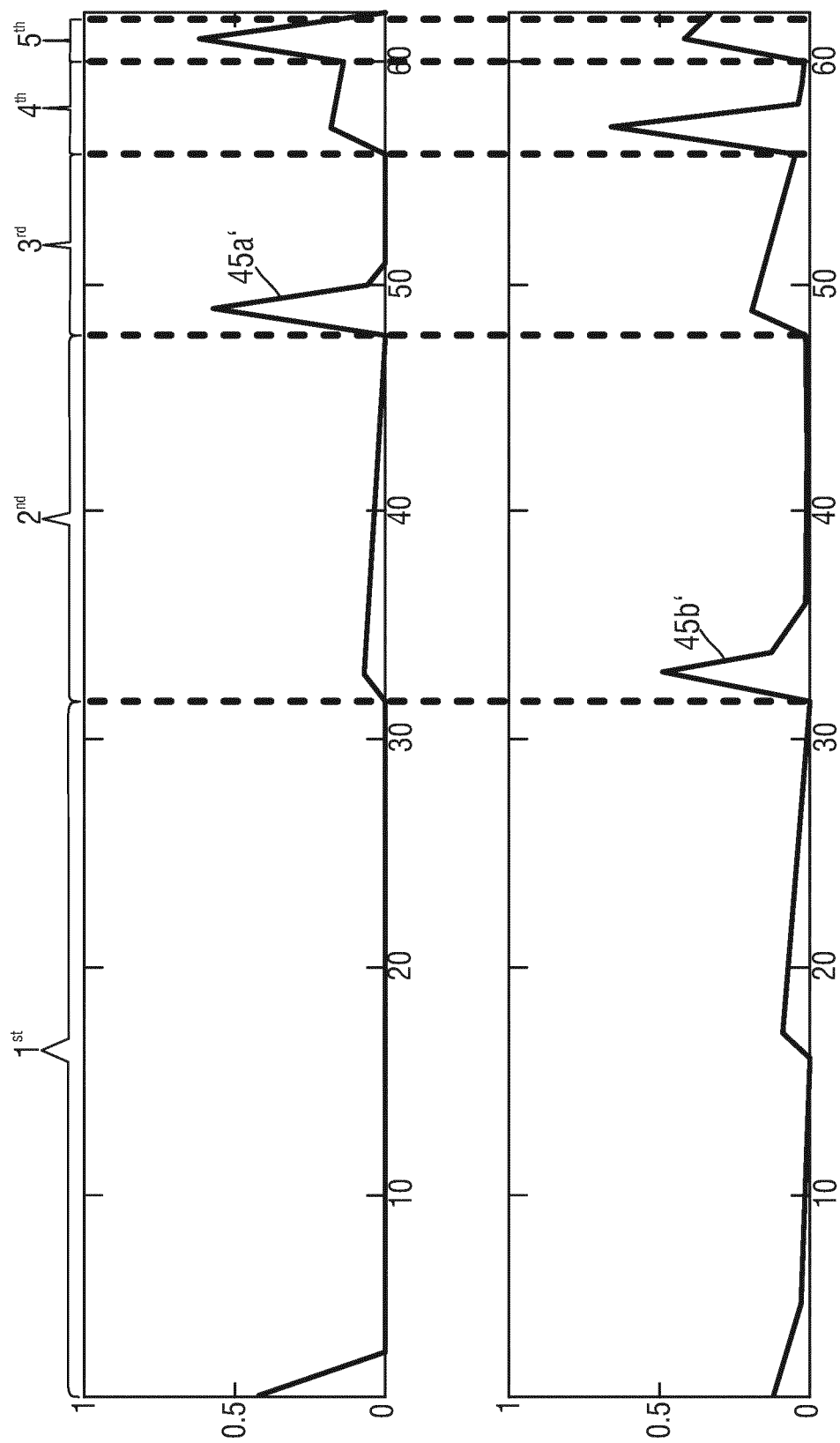
FIG. 9 shows a diagram illustrating descriptors related to the processing according to the second embodiment.

Similarly, the same transformation is further iterated on the transformed signals one or more times. The newly generated patterns in pulse and noise occur in an opposite order, i.e., "peak-flat-peak" versus "flat-peak-flat", as shown in FIG. 9 for an obtained pulse signal descriptor 45a' and a noise signal descriptor 45b'. In the illustrated example the sorted spectral signals of five iterations are concatenated.

In this way, a longer descriptor X is thus created to collect/concatenate the iteratively transformed signals in different scales:

$$X_{i+1}=[X_i,\hat{S}_i^{L/(2\times i)}], \{i|i\in\mathbb{Z}, 1\le i\le\log_2(L)\}, \quad (5)$$

where $\hat{S}_i^{L/(2\times i)}$ is the transformed signal in i-th iteration with length $L/(2\times i)$. When the iteration is finished, the complete descriptor may further be normalized by L2-norm. In fact, the proposed descriptor is built on the hypothesis that multiscale iterations can improve the discriminativity of the descriptor. Such hypothesis has been experimentally verified.

Thus, the iteration acting on the output of the previous iteration is preferably started after halving the length of the signal, in particular partitioning the spectral signal into an in-band and an out-band sub-signal. In this case, the iteration makes a multi-scale representation of the spectrum available to the classifier. Particularly the first iteration leads to a relatively peaked signal representing the non-tissue, due to the elimination of the phase in the noise frequency components. For this reason, at least two sequential transforms may be performed: FFT—delete phase—normalize—rank—

FFT-delete phase—normalize—rank, where for efficiency the second transform may act on the half spectrum obtained from the first iteration.

Figure 10A:
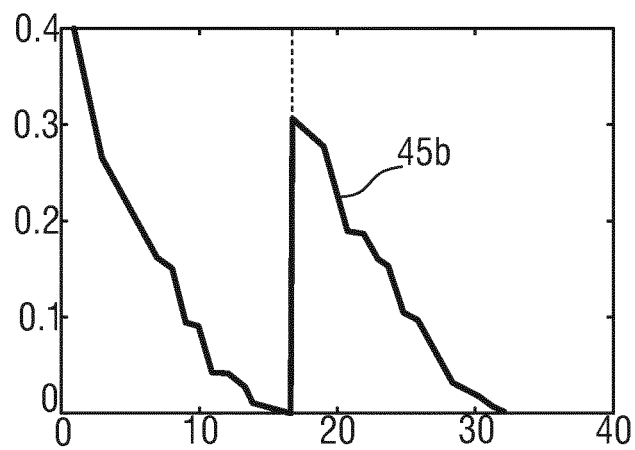
FIGS. 10A and 10B show diagrams illustrating descriptors related to the processing according to a third embodiment of the present invention.
Figure 10B:
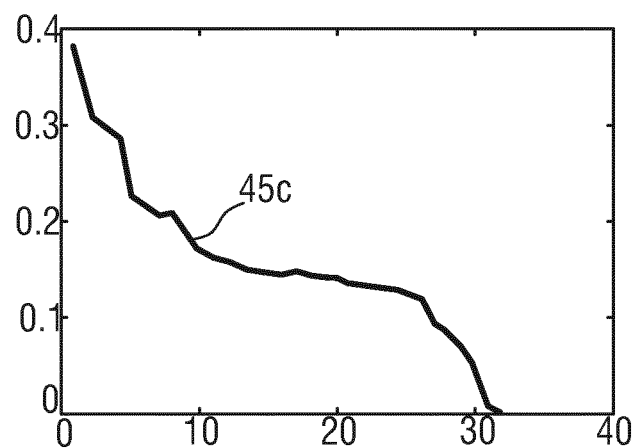

Furthermore, the discriminativity between pulse and noise representations may be further improved. In an embodiment the flat/peaked patterns in the transformed descriptor (45a', 45b') can be made even more flat/peaked. Equation (2) uses a single signal to derive the power spectrum. This may be improved by using two temporally adjacent signals (with one frame shifted). It mainly benefits the noise class: the conjugation of two noise signals induces negative entries in the real part of the power spectrum. This is due to the high-frequency components in noise signals, i.e., background (non-skin) signals are mostly white noise and thus exploited here. Subtracting the minimal negative value in the spectrum can make the noise descriptor more flat in the first iteration, as shown in FIG. 10B showing the thus obtained noise descriptor 45c compared to the original noise descriptor 45b shown in FIG. 10A (and FIG. 5). Therefore, in such an embodiment the boosting step may be modified by conjugating two temporally adjacent signals (with one frame shifted) instead of a single signal.

As illustrated above, in a preferred embodiment, it is proposed to disregard the phase information, but to take the absolute spectrum or the power spectrum.

Preferably, the ranking is done twice: an in-band ranking and an out-band ranking. In-band can simply be the lower half of an oversampled signal, and out-band the upper-half. However, in a more sophisticated version, in-band may be defined as a window around the highest frequency peak, e.g. with half of the total bin-number, out-band then is formed by the remaining frequency bins.

The classification may use a classifier obtained from supervised learning (e.g. AdaBoost, SVM, etc.), taking the samples of the transformed signal as input (e.g. ranked, normalized frequency bins without phase information) and outputting a signal (hard (binary) label, or regression values) identifying the likelihood of an image segment to be alive-human-tissue or not. Although the supervised learning may use actual data obtained from skin and non-skin surfaces, good performance has been obtained by training the classifier using a dataset of 1D time signals including sinusoids with varying amplitudes, levels of noise, and frequencies in the pulse-rate band to represent the segments containing alive human tissue and noise signals (zero-mean Gaussian, or uniform, etc.) representing segments that do not contain alive-human-tissue.

Still further, the proposed method may be applied to classify image regions obtained from segmentation, where possibly motion tracking may be used to track individual segments over time in successive image.

The present invention is preferably applied in the field of rPPG for the acquisition of vital signs of the person. Thus, images obtained by an imaging unit are not only used for detecting skin areas as explained above, but from detected (and preferably tracked, also by use of the present invention) skin areas PPG signals are derived, which are used for deriving vital signs of the person, such as heartbeat, SpO2, etc. The imaging unit 18 is at least sensitive at the wavelength(s) or wavelength ranges, in which the scene is illuminated (by ambient light and/or by illumination), but may be sensitive for other wavelengths as well, in particular if required for obtaining the desired vital signs.

In another embodiment of the present invention, the proposed analysis for skin detection can be combined with another method for skin detection, e.g. the analysis of chrominance or temporal pulsatility of structured light reflected from the skin area as generally known. The method may comprise further steps and may be modified as explained above for the various embodiments of the device and as disclosed herein.

The proposed device and method can be used for continuous unobtrusive monitoring of PPG- or motion-related vital signs (e.g. heartbeat, SpO2, respiration), and can be used in NICU, Operation Room, or General Ward. The proposed device and method can be also used for personal, e.g. vascular-, health monitoring. Generally, the present invention can be used in all applications where pulsatility needs to be detected in an image of a scene and in particular where skin needs to be distinguished from non-skin.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for remote pulsatility detection comprising one or more processors, the one or more processors comprising:
   an input interface for obtaining image data of a scene, said image data comprising a time sequence of image frames,
   an extractor for extracting a time-varying signal indicative of a periodic physiological phenomenon from a region of interest of said image data,
   a transformer for transforming said time-varying signal into a spectral signal,
   a partitioner for partitioning the spectral signal into at least an in-band sub-signal covering a first frequency range of said spectral signal and an out-band sub-signal covering a second frequency range of said spectral signal, wherein said first frequency range comprises at least a frequency range of the periodic physiological phenomenon, and wherein the first frequency range and the second frequency range are non-overlapping, and further wherein the spectral data is processed before partitioning, and the partitioning is achieved without band-pass filters,
   an analyzer for separately deriving an in-band measure from the in-band sub-signal and an out-band measure from the out-band sub-signal, the in-band measure representing a first descriptor and the out-band measure representing a second descriptor, and
   a classifier for classifying said region of interest as a pulsatile region of a living being or as a non-pulsatile region based on the first and second descriptors, wherein the out-band measure is indicative of non-pulsatility and wherein the classifier is configured to classify said region of interest as the pulsatile region of the living being or as the non-pulsatile region based on a comparison of said out-band measure with said in-band measure.

2. The device as claimed in claim 1,
wherein said time-varying signal is one of a photoplethysmography (PPG) signal, a motion signal indicative of the periodic physiological phenomenon, a ballistocardiography (BC G) signal.

3. The device as claimed in claim 1, wherein said device is a device for skin detection and wherein said classifier is configured to classify said region of interest as a skin region of a living being or as a non-skin region based on the descriptor.

4. The device as claimed in claim 1,
wherein said transformer is configured to transform said time-varying signal into a spectral signal without phase information, wherein the spectral signal is an absolute spectrum.

5. The device as claimed in claim 1,
wherein the analyzer comprises a sorter for separately sorting said in-band sub-signal and said out-band sub-signal to obtain a sorted in-band sub-signal as the in-band measure and a sorted out-band sub-signal as the out-band measure.

6. The device as claimed in claim 1,
wherein the analyzer is configured to separately determine a spectral flatness of the in-band signal as the in-band measure and a spectral flatness of the out-band signal as the out-band measure.

7. The device as claimed in claim 1,
wherein the analyzer is configured to separately determine the in-band measure based on an energy of frequency bins of the in-band signal, and the out-band measure based on an energy of frequency bins of the out-band signal.

8. The device as claimed in claim 1,
wherein the analyzer is configured to separately determine the in-band measure and the out-band measure based on statistical outlier detection.

9. The device as claimed in claim 1,
wherein the out-band measure is indicative of non-pulsatility and wherein the classifier is configured to determine a decision threshold for classifying said region of interest as the pulsatile region of the living being or as the non-pulsatile region based on the out-band measure.

10. The device as claimed in claim 1,
wherein the classifier is further configured to determine a consistency metric of the classification of said region of interest as the pulsatile region of the living being or as the non-pulsatile region.

11. The device as claimed in claim 1,
wherein said partitioner is configured to divide said spectral signal such that the in-band sub-signal covers a lower portion of the frequency range of said spectral signal or a portion of the frequency range around a highest frequency peak of said spectral signal.

12. A system for pulsatility detection comprising:
an imager for acquiring image data of a scene; and
the device for pulsatility detection as defined in claim 1 based on the acquired image data of the scene.

13. A method for remote pulsatility detection comprising:
obtaining, via a processor, image data of a scene, said image data comprising a time sequence of image frames,
extracting a time-varying signal indicative of a periodic physiological phenomenon from a region of interest of said image data,
transforming said time-varying signal into a spectral signal,
partitioning the spectral signal into at least an in-band sub-signal covering a first frequency range of said spectral signal and an out-band sub-signal covering a second frequency range of said spectral signal, wherein said first frequency range comprises at least a frequency range of the periodic physiological phenomenon, and wherein the first frequency range and the second frequency range are non-overlapping, and further wherein the spectral data is processed before partitioning, and the partitioning is achieved without band-pass filters,
separately deriving an in-band measure from the in-band sub-signal and an out-band measure from the out-band sub-signal, the in-band measure representing a first descriptor and the out-band measure representing a second descriptor, and
classifying said region of interest as a pulsatile region of a living being or as a non-pulsatile region based on the first and second descriptors, wherein the out-band measure is indicative of non-pulsatility and wherein the classifier is configured to classify said region of interest as the pulsatile region of the living being or as the non-pulsatile region based on a comparison of said out-band measure with said in-band measure.

14. A non-transitory computer-readable medium that stores therein a computer program product, which when executed on a processor, causes the processor to:
obtain image data of a scene, said image data comprising a time sequence of image frames,
extract a time-varying signal indicative of a periodic physiological phenomenon from a region of interest of said image data,
transform said time-varying signal into a spectral signal,
partition the spectral signal into at least an in-band sub-signal covering a first frequency range of said spectral signal and an out-band sub-signal covering a second frequency range of said spectral signal, wherein said first frequency range comprises at least a frequency range of the periodic physiological phenomenon, and wherein the first frequency range and the second frequency range are non-overlapping, and further wherein the spectral data is processed before partitioning, and the partitioning is achieved without band-pass filters,
separately derive an in-band measure from the in-band sub-signal and an out-band measure from the out-band sub-signal, the in-band measure representing a first descriptor and the out-band measure representing a second descriptor, and
classify said region of interest as a pulsatile region of a living being or as a non-pulsatile region based on the first and second descriptors, wherein the out-band measure is indicative of non-pulsatility and wherein the classifier is configured to classify said region of interest as the pulsatile region of the living being or as the non-pulsatile region based on a comparison of said out-band measure with said in-band measure.

15. The method as claimed in claim 13, wherein said time-varying signal is one of a photoplethysmography (PPG) signal, a motion signal indicative of the periodic physiological phenomenon, a ballistocardiography (BCG) signal.

16. The method as claimed in claim 13, wherein the step of transforming is without phase information, wherein the spectral signal is an absolute spectrum.

* * * * *